United States Patent [19]

Kort et al.

[11] 4,452,794
[45] Jun. 5, 1984

[54] MEDICINE HAVING TRANSPLANT REJECTION AND/OR IMMUNOLOGICAL INFLAMMATION INHIBITING ACTIVITIES, AS WELL AS A METHOD FOR INHIBITING TRANSPLANT REJECTION AND/OR IMMUNOLOGICAL INFLAMMATION

[75] Inventors: Willy J. Kort, Euenbergen; Ivan L. Bonta, Rotterdam; Martinus J. P. Adolfs, Capelle ald Yssel; Dirk L. Westbroek, The Hague, all of Netherlands

[73] Assignee: Erasmus Universiteit Rotterdam, Rotterdam, Netherlands

[21] Appl. No.: 448,332

[22] Filed: Dec. 9, 1982

[30] Foreign Application Priority Data

Dec. 15, 1981 [NL] Netherlands .................. 8105635

[51] Int. Cl.³ .......................................... A01N 45/00
[52] U.S. Cl. ................................. 424/240; 424/269; 424/250
[58] Field of Search ............... 424/242, 243, 240, 269

[56] References Cited

U.S. PATENT DOCUMENTS 4,198,405 4/1980 Enomoto et al. .................. 424/243
4,318,908 3/1982 Enomoto et al. .................. 424/243

*Primary Examiner*—Elbert L. Roberts
*Attorney, Agent, or Firm*—Kane, Dalsimer, Kane, Sullivan and Kurucz

[57] ABSTRACT

A medicine having transplant rejection and/or immunological inflammation inhibiting activities is provided, said medicine comprising a combination of a prostaglandin derivative and an immunosuppressive drug, such as a corticosteroid or a mercaptopurine, whereas further a method for treating patients is provided.

13 Claims, No Drawings

MEDICINE HAVING TRANSPLANT REJECTION AND/OR IMMUNOLOGICAL INFLAMMATION INHIBITING ACTIVITIES, AS WELL AS A METHOD FOR INHIBITING TRANSPLANT REJECTION AND/OR IMMUNOLOGICAL INFLAMMATION

The invention relates to a medicine having transplant rejection and/or immunological inflammation inhibiting activities. Further the invention relates to a method for inhibiting the rejection of a transparent and/or inhibiting immunological inflammation in patients.

A serious problem after transplantation of a donor organ in a receiving organism is the occurrence of an immunoreaction of the receiving organism towards the allograft leading finally to the rejection of the transplant and the annihilation of the effected surgery. In order to prevent transplant rejection the patient is treated with corticosteroids and/or other immunosuppressive drug. Both classes of medicines show however a number of very undesirable side-effects, such as for example the promotion of viral, bacterial and fungal infections. Besides, a prolonged therapy with corticosteroids may eventually lead to osteoporosis, diabetes, suppression of adrenal function, gastric hemorrhages, and psychotic disorders.

Therefore, a dose reduction of the immunosuppressive therapy will lead to an improvement of the morbidity and mortality of the patient. Although classical immunosuppressive drugs, such as azathioprine and prednisolone, are clinically used for suppressing the rejection of transplants these appear to be insufficiently adequate.

It is known from animal studies, that prostaglandins have certain immunoreactive properties. For example, prostaglandins may suppress the formation of antibodies in B-lymphocytes, may prevent lysosomal enzyme release, may suppress macrofagal functions and may act as local feedback inhibitors on T-cell activity. Moreover, an increased cellular immunoreactivity is observed when the prostaglandin synthesis is blocked.

Unexpectedly, it was found that prostaglandin derivatives combined with classical immunosuppressive drugs showed strongly increased immunosuppressive activities and could promote significantly the inhibition of transplant rejection. Moreover, the same combination of drugs could significantly increase the inhibition of a proliferative immunological inflammation.

Therefore, according to the invention the medicine as described above, is characterized in that the medicine includes a mixture of a natural or synthetic prostaglandin or prostaglandin derivative and a natural or synthetic substance having immunosuppressive activities as the active component, as well as pharmacologically acceptable carriers and/or vehicles.

It was shown in rat studies, that the combination of a prostaglandin derivative and a substance having immunosuppressive activities shows a special synergistic action. Whereas the survival time of heart transplants was 7 to 10 days without immunosuppressive treatment, and could not significantly be prolonged by treatment with either a prostaglandin derivative or a substance having immunosuppressive activities, a prolonged transplant survival up till 60 days could be observed when the combination of drugs according to the invention was administered. Furthermore, neither a substance having immunosuppressive actions, such as prednisolone, nor the prostaglandin derivative, when separately administered in a low dose, could suppress the granulomatous inflammation, whereas a significant reduction of the granuloma dry weight was obtained by means of the combination of drugs according to the invention.

According to the invention a synthetic, long-term active prostaglandin, (15S)-15-methyl-PGE$_1$, being an orally administrable prostaglandin analogue having a half-life several times larger than that of a natural prostaglandin, has proven to be particularly suitable.

However, it is to be appreciated that other prostaglandin derivatives being able for example to increase the cyclic AMP level in lymphocytes and macrofages are also suitable.

The medicine according to the invention may include any prior art immunosuppressive drug, such as for example corticosteroids, as the substance having immunosuppressive activities. The corticosteroid prednisolone, but also an other immunosuppressive drug as azathioprine are specially mentioned.

It should however be appreciated that other corticosteroids and other immunosuppressive drugs outside the class of corticosteroids will have a comparable beneficial activity.

The medicine according to the invention contains the prostaglandin derivatives and the substance having immunosuppressive activities in a weight proportion of from 4:1 to 1:64, preferably in a proportion of 1:4 to 1:8.

The medicine according to the invention is adequately administered in such a dose, that the patient daily receives 0.13 mg/kg to 1.2 mg/kg of the prostaglandin derivative and 0.3 mg/kg to 8.0 mg/kg of the substance having immunosuppressive activities. For inhibition of the transplant rejection doses of 0.3 mg/kg per day to 1.0 mg/kg per day of the prostaglandin derivative and 2.4 mg/kg per day to 8.0 mg/kg per day of the corticosteroid, as well as 0.3 mg/kg per day to 1.0 mg/kg per day of the prostaglandin derivative and 1.2 mg/kg per day to 4.0 mg/kg per day of the non-corticosteroid substance having immunosuppressive activities are preferred. For the treatment of chronic immunological inflammations comparable doses will suffice.

Apart from the active combination with strong synergistic effect, the medicine according to the invention contains conventional pharmaceutically acceptable carriers and/or vehicles, dependent of the administration form, such as tablets for oral administration or solutions or suspensions for injection purposes.

The present medicines may be administered both orally in the form of a tablet and by injection as a solution or suspension.

The invention will now be further elucidated by means of the following non-limiting examples.

EXAMPLE I

Highly inbred male Brown Norway (BN) and Wistar (WR) rats were obtained from the University Animal Breeding Center of the University of Rotterdam. In the heart transplantations the BN rat was used as a donor, the WR rate as a recipient. Transplantations were carried out according to the method of Ono and Lindsey (J. Thorac. Cardiovasc. Surg. (1969) 57, 225–229). The end point was established by means of palpatation of the heart which was placed in the abdomen; when no beating of the transplant could be detected anymore, the transplant was considered to be rejected. When no immunosuppressive treatment was given, uniformly rejection of the transplant occurred within 10 days.

After transplantation, a series of rats were treated with either 4 mg/kg/day of azathioprine, or 8 mg/kg/day of prednisolone, or 1 mg/kg/day of (15S)-15-methyl-PGE$_1$, respectively. Only treatment with prednisolone caused a slight increase of the survival time of the transplants.

In other groups of rats, treatment with the medicine according to the invention by administering a combination of 1 mg/kg/day of (15S)-15-methyl-PGE$_1$ and 4 mg/kg/day of azathioprine, or a combination of 1 mg/kg/day of (15S)-15-methyl-PGE$_1$ and 8 mg/kg/day of predinisolone, was given respectively. In both cases the survival time was increased significantly.

The results are summarized in Table A, from which it appears that, though the maximum increase of the median survival time with respect to the control group was only 3 days for treatment with one of the separate components of the synergistically active combination according to the invention, this increase was 8.5 days and 17.5 days, respectively, in the treatment with the medicines according to the invention.

TABLE A

| BN→WR heart transplant survival time | | |
|---|---|---|
| Treatment | Survival time (days) | Median |
| control | 7,7,8,8,8,8,8,9,10,10 | 8 |
| (15S)-15-methyl-PGE$_1$ | 8,8,9,9,9,9,10,10,11,15 | 9 |
| prednisolone | 9,9,10,11,11,13,13,15,16,21 | 12 |
| prednisolone + (15S)-15-methyl-PGE$_1$ | 8,13,16,19,23,28,29,42,56,60 | 25.5 |
| azathioprine | 7,8,8,8,8,8,9,9,10,12 | 8 |
| azathioprine + (15S)-15-methyl-PGE$_1$ | 9,11,13,14,15,18,21,25,25,25,40. | 16.5 |

EXAMPLE II

In this example exclusively WR rats were used. Inflammation was induced by implanting polyether sponges impregnated with carrageenan into the back of the rats. Prednisolone was given daily in doses of 0.1 mg/kg and 0.3 mg/kg, whereas (15S)-15-methyl-PGE$_1$ was administered in a dose of 0.25 mg/kg. The rats were killed on the eighth day and the granuloma dry weight was determined as standard of the inhibitory capacity of the medicines.

The results of this experiment are mentioned in Table B.

TABLE B

| Carrageenan-induced granulomatous inflammation | | |
|---|---|---|
| Treatment | Doses | % Inhibition |
| prednisolone | 0.1 mg/kg | 0 |
| (15S)-15-methyl-PGE$_1$ | 0.25 mg/kg | 0 |
| prednisolone + | 0.1 mg/kg + | 19 |
| (15S)-15-methyl-PGE$_1$ | 0.25 mg/kg | |
| prednisolone + | 0.3 mg/kg + | 19 |
| (15S)-15-methyl-PGE$_1$ | 0.25 mg/kg | |

EXAMPLE III

The medicine according to the invention in the form of a tablet was prepared by mixing thoroughly the following ingredients and pressing to a tablet of 200 mg:

| | |
|---|---|
| prednisolone | 72 mg |
| (15S)-15-methyl-PGE$_1$ | 9 mg |
| conventional fillers | 119 mg |
| and/or flavourings | |

EXAMPLE IV

The medicine according to the invention in the form of an injection liquid was prepared by a suppleting a lyophilized preparation consisting of 50 mg of azathioprine and 12.5 mg of (15S)-15-methyl-PGE$_1$ with 10 ml of sterile water.

We claim:

1. Pharmaceutical composition having transplant rejection and/or immunological inflammation inhibiting activities, characterized in that the pharmaceutical composition includes a mixture of a natural or synthetic prostaglandin or prostaglandin derivative and a natural or synthetic substance having immunosuppressive activities as active component, as well as pharmacologically acceptable carriers and/or vehicles.

2. Pharmaceutical composition according to claim 1, characterized in that it contains (15S)-15-methyl-PGE$_1$ as the prostaglandin derivative.

3. Pharmaceutical composition according to claim 1, characterized in that the substance having immunosuppressive activities is a corticosteroid.

4. Pharmaceutical composition according to claim 3, characterized in that the substance having immunosuppressive activities is prednisolone.

5. Pharmaceutical composition according to claim 1, characterized in that the substance having immunosuppressive activities is a mercaptopurine.

6. Pharmaceutical composition according to claim 5, characterized in that the substance having immunosuppressive activities is azathioprine.

7. Pharmaceutical composition according to any one of claims 1–4, characterized in that it contains a mixture of (15S)-15-methyl-PGE$_1$ and prednisolone.

8. Pharmaceutical composition according to claim 1, 2, 5 or 6, characterized in that it contains a mixture of (15S)-15-methyl-PGE$_1$ and azathioprine.

9. Pharmaceutical composition according to any one of claims 1–8, characterized in that it contains the prostaglandin derivative and the substance having immunosuppressive activities in a weight proportion of from 4:1 to 1:64.

10. Pharmaceutical composition according to claim 9, characterized in that it contains the prostaglandin derivative and the substance having immunosuppressive activities in a weight proportion of 1:4 to 1:8.

11. Method for inhibiting the rejection of a transplant and/or for inhibiting immunological inflammation with a patient, characterized in that a pharmaceutical composition according to any one of according to claims 1–10 is administered to the patient in a form and dose suitable for therapeutical purposes.

12. Method according to claim 11, characterized in that the prostaglandin derivative is administered in doses of from 0.13 mg/kg/day to 1.2 mg/kg/day and the substance having immunosuppressive activities in doses of from 0.3 mg/kg/day to 0.8 mg/kg/day.

13. Method according to claim 11 or 12, characterized in that the pharmaceutical composition is administered in doses of from 0.3 mg/kg/day to 1.0 mg/kg/day of the prostaglandin derivative and from 2.4 mg/kg/day to 8.0 mg/kg/day of the corticosteroid, and in doses of from 0.3 mg/kg/day to 1.0 mg/kg/day of the prostaglandin derivative and from 1.2 mg/kg/day to 4.0 mg/kg/day of the non-corticosteroid substance having immunosuppressive activities, respectively.

* * * * *